(12) United States Patent
Shankarappa et al.

(10) Patent No.: US 9,408,846 B2
(45) Date of Patent: Aug. 9, 2016

(54) FORMULATIONS AND METHODS FOR DELAYING ONSET OF CHRONIC NEUROPATHIC PAIN

(71) Applicant: The Children's Medical Center Corporation, Boston, MA (US)

(72) Inventors: Sahadev Aramanethalgur Shankarappa, Bangalore (IN); Daniel S. Kohane, Newton, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/396,316

(22) PCT Filed: Apr. 23, 2013

(86) PCT No.: PCT/US2013/037838
§ 371 (c)(1),
(2) Date: Oct. 22, 2014

(87) PCT Pub. No.: WO2013/163214
PCT Pub. Date: Oct. 31, 2013

(65) Prior Publication Data
US 2015/0079159 A1 Mar. 19, 2015

Related U.S. Application Data

(60) Provisional application No. 61/637,156, filed on Apr. 23, 2012.

(51) Int. Cl.
| *A61K 31/519* | (2006.01) |
| *A61K 31/573* | (2006.01) |
| *A61K 45/06* | (2006.01) |
| *A61K 9/00* | (2006.01) |
| *A61K 9/127* | (2006.01) |

(52) U.S. Cl.
CPC ............. *A61K 31/519* (2013.01); *A61K 9/0019* (2013.01); *A61K 9/1272* (2013.01); *A61K 31/573* (2013.01); *A61K 45/06* (2013.01)

(58) Field of Classification Search
CPC ...................................................... A61K 9/127
USPC ....................................................... 424/450
See application file for complete search history.

(56) References Cited

U.S. PATENT DOCUMENTS

| 5,650,428 | A | | 7/1997 | Ohmori | |
| 5,747,060 | A | * | 5/1998 | Sackler | A61K 31/165 424/426 |
| 5,776,488 | A | * | 7/1998 | Mori | A61K 9/127 424/450 |
| 6,326,020 | B1 | * | 12/2001 | Kohane | A61K 31/135 424/426 |
| 6,803,053 | B2 | * | 10/2004 | Papahadjopoulos | A61K 9/0019 424/450 |
| 2012/0027844 | A1 | | 2/2012 | Beckman | |
| 2012/0034296 | A1 | | 2/2012 | Epstein-Barash et al. | |

FOREIGN PATENT DOCUMENTS

| WO | 9851290 | 11/1998 | |
| WO | WO 98/51290 | 11/1998 | |
| WO | 2010117996 | 10/2010 | |
| WO | WO 2010/117996 | 10/2010 | |
| WO | WO 2010117996 A1 * | 10/2010 | ............. A61K 31/02 |

OTHER PUBLICATIONS

Childrens Medical Center Publications Aboul-Fadl, "Antisense oligonucleotides: the state of the art", *Curr Med Chem.*,12:2193-214 (2005).
Alam, et al., "Design of liposome to improve encapsulation efficiency of gelonin and its effect on immunoreactivity and ribosome inactivating property", *Mol Cell Biochem.*, 112:97-107 (1992).
Barnet, et al., "Tissue injury from tricyclic antidepressants used as local anesthetics", *Anesth Analg*, 101(6):1838-43 (2005).
Befort, et al., "Selective up-regulation of the growth arrest DNA damage-inducible gene Gadd45 alpha in sensory and motor neurons after peripheral nerve injury", *Eur J Neurosci.*, 18(4):911-22 (2003).
Chaim-Matyas, et al., "Encapsulation of the cobra cytotoxin P4 in liposomes", *Biotechnol Appl Biochem.*, 17( Pt 1): 31-6 (1993).

de Paiva and Dolly, "Light chain of botulinum neurotoxin is active in mammalian motor nerve terminals when delivered via liposomes", *FEBS Lett.*, 277:171-4 (1990).

Drager, et al., "Prolonged intercostal nerve blockade in sheep using controlled-release of bupivacaine and dexamethasone from polymer microspheres", *Anesthesiology*, 89(4):969-79.

Freitas and Frezard, "Encapsulation of native crotoxin in liposomes: a safe approach for the production of antivenom and vaccination against Crotalus durissus terrificus venom", *Toxicon.*, 35:91-100 (1997).

Gregoriadis and Allison, "Entrapment of proteins in liposomes prevents allergic reactions in pre-immunised mice", *FEBS Lett.*, 45:71-4 (1974).

Gregoriadis and Ryman, "Liposomes as carriers of enzymes or drugs: a new approach to the treatment of storage diseases" *Biochem J.*, 124:58P (1971).

Gregoriadis, et al., "Improving the therapeutic efficacy of peptides and proteins: a role for polysialic acids", *Int J Pharm*, 300:125-30 (2005).

Gregoriadis, "Engineering liposomes for drug delivery: progress and problems", *Trends Biotechnol.*, 13:527-37 (1995).

Harden, "Chronic neuropathic pain, mechanisms, diagnosis and treatment", *Neurologist*, 11(2):111-22 (2005).

(Continued)

*Primary Examiner* — Frederick Krass
*Assistant Examiner* — Amanda Heyes
(74) *Attorney, Agent, or Firm* — Pabst Patent Group LLP

(57) ABSTRACT

A dosing regimen for formulations that contain a therapeutic dosage of a site 1 sodium channel blocker, where the dosing regimen provides a prolonged nerve block and is in an effective amount to delay the onset of neuropathic pain, such as hyperalgesia and/or allodynia, for at least one week, and preferably longer at the site, and preferably the region (e.g. entire limb), where the nerve block was applied. The site 1 sodium channel blocker is preferably saxitoxin (STX), preferably in combination with a corticosteroid, preferably dexamethasone. In a preferred embodiment, liposomes are included in the formulation as a controlled release system, producing prolonged duration of block without systemic toxicity. As demonstrated by the examples, encapsulating STX in a controlled release system, such as liposomes, preferably also including a corticosteroid, and administering in suitable dosing regimen to achieve a prolonged nerve block without systemic toxicity, delays the onset of hyperalgesia.

23 Claims, 4 Drawing Sheets

(56) References Cited

OTHER PUBLICATIONS

Jia, et al., "Prolongation of sciatic nerve blockade by in situ cross-linked hyaluronic acid", *Biomaterials*, 25(19):4797-804 (2004).
Kohane, et al, "Prolonged duration local anesthesia from tetrodotoxin-enhanced local anesthetic microspheres", *Pain*, 104(1-2):415-21 (2003).
Kohane, et al., "A re-examination of tetrodotoxin for prolonged duration local anesthesia", *Anesthesiology*, 89(1):119-31 (1998).
Kohane, et al., "Biocompatibility of lipid-protein-sugar particles containing bupivacaine in the epineurium", *J Biomed Mater Res.*, 59(3):450-9 (2002).
Luo, et al., "Injury type-specific calcium channel alpha 2 delta-1 subunit up-regulation in rat neuropathic pain models correlates with antiallodynic effects of gabapentin", *J Pharmacol Exp Ther.*, 303(3):1199-205 (2002).
Mandal and Lee, "Listeriolysin 0-liposome-mediated cytosolic delivery of macromolecule antigen in vivo: enhancement of antigen-specific cytotoxic T lymphocyte frequency, activity, and tumor protection", *Biochim Biophys Acta*, 1563:7-17 (2002).
Nakagomi, et al., "Expression of the activating transcription factor 3 prevents c-Jun N-terminal kinase-induced neuronal death by promoting heat shock protein 27 expression and Akt activation", *J Neurosci.*, 23(12):5187-96 (2003).
Newton, et al., "Dorsal root ganglion neurons show increased expression of the calcium channel alpha2delta-1 subunit following partial sciatic nerve injury", *Brain Res Mol Brain Res.*, 95(1-2):1-8 (2001).
Olivera, et al., "Diversity of Conus neuropeptides", *Science*, 249:257-63 (1990).
Padera, et al., "Local myotoxicity from sustained release of bupivacaine from microparticles", *Anesthesiology*, 108(5):921-8 (2008).
Pere, et al., "Local myotoxicity of bupivacaine in rabbits after continuous supraclavicular brachial plexus block", *Reg Anesth*, 18(5):304-7 (1993).
Sakura, et al., "Local anesthetic neurotoxicity does not result from blockade of voltage-gated sodium channels", *Anesth Analg*, 81(2):338-46 (1995).
Sapra, et al., "Ligand-targeted liposomes for cancer treatment", *Curr Drug Deliv.*, 2:369-81 (2005).
Shankarappa, et al., "Lipsome-encapsulated saxitoxin in the treatment of nerve injury-induced chronic neuropathic pain", *41st Annual meeting of the

Total nerve block duration = 18.1 ± 3.4 days

FORMULATIONS AND METHODS FOR DELAYING ONSET OF CHRONIC NEUROPATHIC PAIN

CROSS REFERENCE TO RELATED APPLICATIONS

This application is a 371 application of International Application No. PCT/US2013/037838, filed Apr. 23, 2013, which claims the benefit of and priority to U.S. Provisional Application No. 61/637,156, filed Apr. 23, 2012.

GOVERNMENT SUPPORT

This invention was made with government support under Grant No. R01GM073626 awarded by the National Institutes of Health. The government has certain rights in the invention.

FIELD OF THE INVENTION

This relates generally to methods and compositions for delaying the onset of chronic neuropathic pain.

BACKGROUND OF THE INVENTION

Pain caused by a primary lesion or dysfunction in the nervous system is defined as neuropathic pain, with nerve trauma, diabetes, multiple sclerosis, HIV infection, and various forms of malignancies being some of the common causes. Approximately 3.75 million cases of chronic neuropathic pain are reported in the United States alone. R. N. Harden, "Chronic Neuropathic Pain: Mechanisms, Diagnosis, and Treatment", The Neurologist, 11: 111 (2005). In addition to patient morbidity, management of chronic neuropathic pain exerts significant burden on health care spending.

Despite the availability of several drugs including opioids, NSAID's and tricyclics, a significant number of patients have unsatisfactory pain control, and may experience undesirable side effects. Enhanced neuronal activity, a prominent feature of neuropathic pain, has been consistently reported in various animal nerve injury models of chronic pain. See, e.g., Coggeshall, et al., "A-fiber sensory input induces neuronal cell death in the dorsal horn of the adult rat spinal cord", J. Comp. Neurol., 435: 276-282 (2001); Govrin-Lippmann, et al., "Ongoing activity in severed nerves: source and variation with time", Brain Res., 159 406-410 (1978); Wu, et al., "Early onset of spontaneous activity in uninjured C-fiber nociceptors after injury to neighboring nerve fibers", Journal of Neuroscience, 21: RC140 (2001).

It has been argued that excitatory neurotransmitters, such as glutamate, released in response to injury-induced aberrant neuronal impulses, leads to calcium mediated excitotoxicity and subsequent cellular injury at the level of the dorsal root ganglion (DRG) and spinal cord. See, e.g., D. W. Choi, "Calcium and Excitotoxic Neuronal Injury", Ann. N.Y. Acad. Sci., 747: 162-171 (2006); Coggeshall, et al., "A-fiber sensory input induces neuronal cell death in the dorsal horn of the adult rat spinal cord", J. Comp. Neurol., 435: 276-282 (2001); C. J. Woolf, "Neuronal Plasticity: Increasing the Gain in Pain", Science, 288:1765-1768 (2000).

However, attempts to block injury-induced neuronal discharges using short-term nerve conduction blockers such as lidocaine and bupivacaine microspheres have been largely unsuccessful. Wen, et al., "Nerve Conduction Blockade in the Sciatic Nerve Prevents but Does Not Reverse the Activation of p38 Mitogen-activated Protein Kinase in Spinal Microglia in the Rat Spared Nerve Injury Model", Anesthesiology, 107: 312-321 (2007); Suter, et al., "Development of neuropathic pain in the rat spared nerve injury model is not prevented by a peripheral nerve block", Anesthesiology, 99(6):1402-8 (2003). In fact, amino-amide local anesthetics themselves, such as bupivacaine and lidocaine, are known to cause neurotoxicity. Gold, et al., "Lidocaine toxicity in primary afferent neurons from the rat", J. Pharmacol. Exp. Ther., 285(2):413-21 (1998); Radwan, et al., "The neurotoxicity of local anesthetics on growing neurons: a comparative study of lidocaine, bupivacaine, mepivacaine, and ropivacaine", Anesth. Analg., 94:319-24 (2002). Long-term nerve blockade and its effect on the onset and maintenance of neuropathic pain are yet to be determined.

The development of local anesthetics to provide prolonged analgesia from a single injection has encountered three principal challenges: (1) inadequate duration of action; (2) systemic toxicity; and (3) adverse local tissue reaction.

A wide variety of controlled-release technologies have been employed to extend the duration of nerve block, but most such systems result at best in a several-fold extension of duration compared to unencapsulated drugs. Approaches that encapsulate synergistic drug combinations have achieved nerve blocks lasting many days. For example, co-encapsulation of bupivacaine and dexamethasone in polymeric microspheres produced nerve blocks lasting more than four days. Drager, et al., Anesthesiology, 89(4):969-979 (1998). Co-encapsulation of site 1 sodium channel blockers (which block the sodium channel at site 1 on the outer surface) with conventional local anesthetics also greatly prolonged sciatic nerve blockade. Addition of dexamethasone prolonged the sciatic nerve blockade to more than nine days in the rat (Kohane, et al, Pain, 104(1-2):415-421 (2003)).

However, tissue reaction to such formulations has been problematic. Conventional local anesthetics are intrinsically myotoxic (Padera, et al., Anesthesiology, 108(5):921-928 (2008); Pere, et al., Reg Anesth, 18(5):304-307 (1993)). They are also myotoxic when released from a wide range of delivery systems (Padera, et al., Anesthesiology, 108(5):921-928 (2008); Jia, et al., Biomaterials, 25(19):4797-4804 (2004)), even when the delivery systems themselves are minimally toxic. The myotoxicity of bupivacaine increases dramatically over extended durations of exposure (Padera, et al., Anesthesiology, 108(5):921-928 (2008)), suggesting that myotoxicity may be an inevitable consequence of sustained release of such compounds.

Conventional local anesthetics are also neurotoxic (Zimmer, et al., Anaesthesist, 56(5):449-453 (2007); Yamashita, et al., Anesth Analg, 97(2):512-519 (2003)). The presence of particles themselves enhances local anesthetic myotoxicity in vivo (Padera, et al., Anesthesiology, 108(5):921-928 (2008), and can cause inflammatory responses at the nerve that may considerably outlast the duration of blockade (Kohane, et al, Pain, 104(1-2):415-421 (2003); Padera, et al., Anesthesiology, 108(5):921-928 (2008); and Kohane, et al., J Biomed Mater Res., 59(3):450-459 (2002)).

U.S. Pat. No. 6,326,020 to Kohane, et al. discloses compositions containing a combination of naturally occurring site 1 sodium channel blockers, with other agents such as local anesthetics, vasoconstrictors, glutocorticoids, or adrenergic drugs for prolonged duration of nerve block. Site 1 sodium channel blockers do not cause myo- or neurotoxicity (Barnet, et al., Pain 110(1-2):432-438 (2004); Sakura, et al., Anesth Analg, 81(2):338-346 (1995)), which makes them desirable for an extended release formulation. U.S. Pat. No. 6,326,020 discloses poly(lactic acid-glycolic acid) microspheres containing TTX (at 0.1% theoretical loading) alone, in a carrier fluid containing epinephrine, which produces nerve block lasting about six hours with an onset of more than one hour. TTX without epinephrine has been shown to produce sciatic nerve block, but with considerable toxicity at the most effective doses (Kohane, et al., Anesthesiology, 89(1):119-131 (1998). Studies by Kohane, et al, *Pain,* 104(1-2):415-421 (2003) employing polymeric microspheres of TTX alone showed that TTX was lethal (at 0.1% w/w) or ineffective for nerve block (at 0.05% w/w), producing a median block of 0 min.

Additionally, it is extremely difficult to encapsulate effectively these extremely potent local anesthetics in polymeric particles since they are hydrophilic and the systemic toxicity from their initial rapid release is dose-limiting (Barnet, et al., *Anesth Analg,* 101(6):1838-1843 (2005); Kohane, et al., *Anesthesiology,* 89(1):119-131 (1998)). This makes the development of particulate systems based entirely on such compounds (i.e. without inclusion of conventional local anesthetics) very difficult.

There is a need for a formulation and/or method for preventing or delaying the onset of neuropathic pain, such as hyperalgesia or allodynia.

It is an object of the present invention to provide a formulation for preventing or delaying the onset of neuropathic pain, such as hyperalgesia or allodynia.

It is still another object of the present invention to provide a method for preventing or delaying the onset of neuropathic pain, such as hyperalgesia or allodynia.

SUMMARY OF THE INVENTION

A dosing regimen for formulations that contains a therapeutic dosage of a site 1 sodium channel blocker is described herein. The dosing regimen provides a prolonged nerve block and after the nerve block ends, the channel blocker is present in an effective amount to delay the onset of neuropathic pain, such as hyperalgesia and/or allodynia, for one week, preferably two weeks, and preferably longer at the site, and preferably the region (e.g. entire limb), where the nerve block was applied.

The formulations contain a site 1 sodium channel blocker, preferably saxitoxin (STX), for use as a local anesthetic with rapid nerve block, improved potency and efficacy, and no local toxicity. In a preferred embodiment, liposomes are employed in the formulations for increased loading of the site 1 sodium channel blocker, producing prolonged duration of block without systemic toxicity. In one embodiment, the compositions contain a site 1 sodium channel blocker alone. In another embodiment, the compositions contain a site 1 sodium channel blocker in combination with a corticosteroid. In a preferred embodiment, the site 1 sodium channel blocker is saxitoxin, preferably in combination with a corticosteroid, where the preferred corticosteroid is dexamethasone. However, alternative controlled release formulations may be used in addition to liposomes, such as micelles, polymeric microparticles, or polymeric nanoparticles.

As demonstrated by the examples, encapsulating STX in liposomes, preferably also including a corticosteroid, and administering in suitable dosing regimen to achieve a prolonged nerve block without systemic toxicity delays the onset of hyperalgesia.

BRIEF DESCRIPTION OF THE DRAWINGS

FIGS. 1A, B and C are graphs of intra-liposome STX content (μg/m1) and mean liposome size (microns) (FIG. 1A), sensory block (FIG. 1B) as a function of withdrawal latency (seconds), and motor block (FIG. 1C) as a function of extensor postural thrust (g) duration (days) from rats administered one 0.3 ml dose of liposomes containing 1.1 mg/ml of STX (referred to herein as "STX-L") as nerve block injection (dark circles) compared to rats that did not receive treatment (open circles) following spared nerve injury (SNI). Data are means with standard deviations (n=5).

FIG. 2 is a graph comparing the M wave and H wave for rats that did not receive treatment ("untreated limb") with rats that were administered one 0.3 ml dose of STX-L as nerve block injection. M wave and H wave latency (ms) and M wave amplitude (mV) are provided. Data are means with standard deviations (n=5).

FIGS. 3A and B are graphs of withdrawal threshold (g) over time (days) for the treated (ipsilateral limb) (FIG. 3A) and untreated limb (contralateral limb) (FIG. 3B) for rats administered 1 dose of STX-L following SNI (SNI+STX liposomes) (open circles) compared to untreated rats (SNI alone) (dark circles). The duration of the nerve block was 7.0 days±1.1 days). Data are provided as means with standard deviations (n=5).

FIGS. 4A, B, C, and D are graphs of withdrawal threshold (g) over time (weeks) for the treated (ipsilateral limb) (FIG. 4A) and untreated limb (contralateral limb) (FIG. 4B); withdrawal latency (seconds) over time (days) for the treated (ipsilateral) limb (FIG. 4C); and body weight (g) over time (weeks) for rats administered three 0.3 ml doses of STX-L following SNI (SNI+STX liposomes (open circles) compared to untreated rats (SNI alone) (dark circles). The duration of the nerve block is depicted in FIG. 4A as a grey box (18.1±3.4 days). Data are provided as means with standard deviations (n=5).

FIGS. 5A and B are bar graphs of % green fibrillary acidic protein (GFAP) positive area (an indicator of astrocyte activation) in lumbar spinal cord harvested from SNI rats at two time periods (day 5 post-operative and day 60 post operative) for three groups: rats without SNI, but administered liposomes alone (without STX) ("Vehicle") (white bar), rats with SNI, but without treatment ("SNI") (black bar) and rats with SNI and treated with STX -L ("SNI+STX liposomes") (grey bar). FIG. 5A shows the results for the ipsilateral limb; and FIG. 5B shows the results for the contralateral limb. Data are provided as means with standard deviations (n=5).

DETAILED DESCRIPTION OF THE INVENTION

I. Definitions

As used herein a site 1 sodium channel blocker is a molecule that binds the outer opening of sodium channels at a location termed "site 1". In a preferred embodiment, the site 1 sodium channel blocker is a naturally occurring toxin or a derivative thereof.

The term "derivative thereof" as used herein includes any derivative of a site 1 sodium channel blocker having substantially the same functional properties as the non-derivatized site 1 sodium channel blocker such as biological and/or pharmacological, i.e. to effectively block sodium channels.

The term "hyperalgesia" as used herein means an increased response to a painful stimulus.

The term "allodynia" as used herein means a painful response to a normally innocuous stimulus.

II. Compositions

The composition is designed to prolong the duration of a local anesthetic block, with no systemic toxicity. The composition contains a Site 1 sodium channel blocker alone or in combination with a corticosteroid, administered in a pharmaceutically acceptable carrier in amounts effective to prolong the duration of block of the local anesthetic, with no systemic toxicity. The composition is administered in a formulation locally at the site where the nerve is to be blocked, preferably as a suspension.

In the preferred embodiment, the carriers are liposomes, however, other controlled release systems, such as micelles, microparticles or nanoparticles can be used.

A. Site 1 Sodium Channel Blockers

Site I sodium channel blockers include tetrodotoxin (TTX), saxitoxin (STX), decarbamoyl saxitoxin, neosaxitoxin, and the gonyautoxins (referred to jointly herein as "toxins"). The preferred toxin is STX.

Saxitoxin, a neurotoxin that is naturally produced by certain species of algae, suppresses neuronal activity by specifically binding to site 1 of neuronal voltage gated sodium channels to produce nerve conduction blocks. Saxitoxin was first extracted from the Alaska butterclam, *Saxidomus gigantcus*, where it is present in algae of the genus *Gonyaulax*. The reported chemical formula is $C_{10}H_{15}N_7O_3.2HCl$. It is believed the toxin has a perhydropurine nucleus in which are incorporated two guanidinium moieties. Saxitoxin is too toxic to be used alone as a local anesthetic.

A number of polypeptides have been isolated from the paralytic venoms of the fish hunting cone snails of the genus *Conus* found in the Philippine archipelago. Designated "conotoxins", these have been discovered to affect ion channel function. The paralytic a, m, and w conotoxins block nicotinic acetylcholine receptors, sodium channels, and voltage sensitive calcium channels, respectively (reviewed in Olivera, et al., *Science,* 249:257-263 (1990)). Those which block sodium channels can be used in the same manner as the tetrodotoxins and saxitoxins.

1. Dosing Regimen

Preferably a suitable dosing regimen is used to provide a prolonged nerve block, i.e. longer than 7 days, preferably longer than 8 days, preferably longer than 10 days, most preferably about 18 days in duration following administration of the first dose of liposomes. Preferably the dosing regimen is also suitable for providing a prolonged delay in the onset of hyperalgesia compared to when the nerve block is not applied. In some embodiments, the dosing regimen is suitable for delaying the onset of allodynia compared to when the nerve block is not applied.

Dosage ranges for STX encapsulated in the carrier are between 28 micrograms and 1.5 mg, preferably with a loading in the carrier, preferably liposomes, of between 0.1 to 90% by weight, more preferably between 5 and 75%.

B. Corticosteroids

Corticosteroids that are useful to prolong in vivo nerve blockade include glucocorticoids such as dexamethasone, cortisone, hydrocortisone, prednisone, and others routinely administered orally or by injection. Other glucocorticoids include beclomethasone, betamethasone, flunisolide, methyl prednisone, para methasone, prednisolone, triamcinolome, alclometasone, amcinonide, clobetasol, fludrocortisone, diflurosone diacetate, fluocinolone acetonide, fluorometha-lone, flurandrenolide, halcinonide, medrysone, and mometasone, and pharmaceutically acceptable salts and mixtures thereof. The relative strengths of the different corticosteriods are well known, and described, for example, in Goodman and Gilman's.

Typically these are administered at between 0.05 and 1 mg dexamethasone/mg, or equivalent based on strength of glucocorticoid (weaker requiring more, stronger requiring less). Preferably, the glucocorticoid is incorporated into the carrier, preferably liposome, in a molar ratio of lipids to glucocorticoid ranging from 10:0.0001 to 1:0.0001, preferably 6:0.0001. Preferably, the glucocorticoid is dexamethasone.

Liposomes containing saxitoxin have been shown to produce prolonged nerve blockade without local toxicity, and in most formulations without systemic toxicity. Although these liposomes did not require synergistic compounds such as bupivacaine and dexamethasone, block duration was greatly extended by their use. See, U.S. Published Application No. 2012-00342096. For example, incorporation of dexamethasone produced blocks lasting more than seven days without any systemic toxicity detectable by neurobehavioral testing methods and clinical exam (Kohane, et al., *Pain.,* 104(1-2): 415-421 (2003)).

C. Carriers

The formulation may include any pharmaceutically acceptable carrier that can deliver the site I sodium channel blocker in a controlled manner, such that a prolonged nerve block, such as greater than 7 days, greater than 8 days, greater than 10 days, greater than 15 days, or approximately 18 days in duration is provided. Suitable carriers include but are not limited to liposomes, micelles, microparticles, and nanoparticles. The site I sodium channel blocker may be attached to the carrier using a suitable ligand, or may be encapsulated in the carrier.

In the preferred embodiment, the carrier is a liposome, stored in a vial as a dry powder, or suspended in an aqueous solution for injection. Liposomes (LPs) are spherical vesicles, composed of concentric phospholipid bilayers separated by aqueous compartments. LPs have the characteristics of adhesion to and creating a molecular film on cellular surfaces. Liposomes are lipid vesicles composed of concentric phospholipid bilayers which enclose an aqueous interior (Gregoriadis, et al., Int J Pharm 300:125-30 2005 (2005); Gregoriadis and Ryman, Biochem J, 124: 58P (1971)). The lipid vesicles comprise either one or several aqueous compartments delineated by either one (unilamellar) or several (multilamellar) phospholipid bilayers (Sapra, et al., Curr Drug Deliv, 2: 369-81 (2005)). The success of liposomes in the clinic has been attributed to the nontoxic nature of the lipids used in their formulation. Both the lipid bilayer and the aqueous interior core of liposomes can serve the purpose of treatment.

Liposomes have been well studied as carrier of toxins for enhancing their efficacy at lower doses (Alam, et al., Mol Cell Biochem 112, 97-107 1992; Chaim-Matyas, et al., Biotechnol Appl Biochem 17 (Pt 1), 31-6 1993; de Paiva and Dolly, FEBS Lett 277, 171-4 (1990); Freitas and Frezard, Toxicon 35, 91-100 (1997); Mandal and Lee, Biochim Biophys Acta 1563, 7-17 (2002)).

Liposomes have been widely studied as drug carriers for a variety of chemotherapeutic agents (approximately 25,000 scientific articles have been published on the subject) (Gregoriadis, N Engl J Med 295, 765-70 (1976); Gregoriadis, et al., Int J Pharm 300, 125-30 (2005)). Water-soluble anticancer substances such as doxorubicin can be protected inside the aqueous compartment(s) of liposomes delimited by the phospholipid bilayer(s), whereas fat-soluble substances such as amphotericin and capsaicin can be integrated into the phospholipid bilayer (Aboul-Fadl, Curr Med Chem 12, 2193-214 (2005); Tyagi, et al., J Urol 171, 483-9 (2004)). Delivery of chemotherapeutic agents using liposomes leads to improved pharmacokinetics and reduced toxicity profile (Gregoriadis, Trends Biotechnol 13, 527-37 (1995); Gregoriadis and Allison, FEBS Lett 45, 71-4 1974; Sapra, et al., Curr Drug Deliv 2, 369-81 (2005)).

1. Phospholipids

Preferred phospholipids are the naturally occurring phospholipids such as 1,2 dimyristoyl-sn-glycero-3-phosphocholine (DMPC), 1,2-distearoyl-sn-glycero-3 phosphocholine (DSPC), 1,2-distearoyl-sn-glycero-3-phosphatidylglycerol, sodium salt (DSPG), and 1,2-dimyristoylsn-glycero-3-phosphglycerol, sodium salt-(DMPG). In the preferred embodiment, liposomes are produced with DMPC and DMPG, or DSPC and DSPG (DMPC=1,2-dimyristoyl-sn-glycero-3-phosphocholine, DMPG=2-dimyristoyl-sn-glycero-3-phosphglycerol, DSPC=1,2-distearoyl-sn-glycero-3-phosphocholine, DSPG=1,2-distearoyl-sn-glycero-3-phosphatidylglycerol). Those made with DMPC are referred to as "fluid" liposomes; those with DSPC as "solid" based on their phase transition temperatures ($T_m$).

2. Pharmaceutically Acceptable Carriers

The compositions can be provided in any pharmaceutically acceptable carrier for injection, such as water for injection, sterile water, saline, dextrose solutions, carboxymethylcellulose, mannitol, and buffered solutions. For topically applied formulations, a suitable carrier for topical application is used.

III. Methods of Administration

The composition can be administered by any of the methods for administering local anesthetics known to one of ordinary skill in the art. The composition can be formulated for topical anesthesia, infiltration anesthesia, filed block anesthesia, nerve block anesthesia, intravenous regional anesthesia, spinal anesthesia, and epidural anesthesia.

Preferably, the composition is formulated for nerve block anesthesia. Typical formulations are suitable for injection or topical administration.

IV. Uses

The dosing regimen described herein can be used to treat, prevent or delay the onset of chronic pain in a patient, such as phantom limb pain, neuropathy, neuropathic pain and/or reflex sympathetic dystrophy.

The present invention will be further understood by reference to the following non-limiting examples.

EXAMPLES

Example 1

Effect of Prolonged Suppression of Neuronal Activity in the Injured Nerve by STX-Containing Liposomes on the Onset of Chronic Pain in the Spared Nerve Injury (SNI) Model Liposome Preparation Liposomes were produced by the thin lipid film technique, using 1,2-distearoyl-sn-glycero-3 phosphocholine (DSPC) and 1,2-distearoyl-sn-glycero-3-phoshatidylglycerol (DSPG) and cholesterol. DSPC:DSPG:cholesterol:dexamethasone (3:1:2:0.0001 molar ratio) were dissolved in a mixture of warm chloroform and methanol (9:1 v/v). The lipid mixture was dried in a rotary evaporator (BUCHI Labortechnik AG, Switzerland) at 60° C., to obtain a thin lipid film layer. The vacuum pressure within the rotary evaporator was maintained at 480 torr for 20 minutes and then gradually decreased to 20 torr over a period of 30 minutes. Warm t-butanol was used to reconstitute the lipid film followed by immediate immersion in liquid nitrogen. The lipid mixture was then lyophilized for at least 24 hours and the resulting lipid cake was hydrated with warm 250 mM ammonium sulfate buffer containing 0.6 mM saxitoxin dihydrochloride (from Dr. Sherwood Hall, FDA, College Park, Md.). The liposome suspension was homogenized at 10,000 rpm using a high shear laboratory mixer (Silverson Machines Inc.), followed by repeated freeze-thaw cycles. Liposomes were then dialysed in 50-kD cut-off dialysis tubing, against 0.9% saline at 4° C. for 48-74 hours to yield a final liposome formulation that did not contain free STX.

The STX liposomes (STX-L) contained 1.1 mg STX/ml formulation and were administered in doses of 0.3 ml.

Liposome Properties

Size of liposomes was determined using a Multisizer 3 Coulter Counter (Beckman Coulter Inc.) Intra-liposome STX content was determined after separating the lipid fraction using the Bligh and Dryer method (E. G. Bligh, W. J. Dyer, *A Rapid Method Of Total Lipid Extraction And Purification*, (1959)). Determination of STX content was based on a previously published method by Bates, et al., "*A chemical assay for saxitoxin. Improvements and modifications*", J. Agric. Food Chem. 26: 252-254 (1978).

Animal Care

This study was conducted using protocols approved by the Committee for Animal Care at the Massachusetts Institute of Technology in accordance with IASP guidelines (M. Zimmermann, *"Ethical guidelines for investigations of experimental pain in conscious animals"*, Pain, 16:109-110 (1983). Adult male Sprague-Dawley rats (Charles River laboratories weighing 400-425 grams were housed in pairs, allowed standard rat diet and water ad libitum, and maintained on a 7 a.m.-7 p.m. light/dark cycle. Animals were randomly divided into groups that either received liposome treatment and/or nerve-injury surgery. Animals that received sham surgeries were used as controls. Rats were euthanized by carbon dioxide inhalation, either on day 5 or day 60 after liposome treatment and/or nerve-injury surgery.

Spared Nerve Injury (SNI)

Rats were anesthetized by 2% isoflurane with 98% oxygen inhalation.

A 3-4 cm skin incision was applied from the left greater trochanter to the knee joint. The muscle layers were separated to expose the sciatic nerve. The trifurcation of the sciatic nerve was identified and the common peroneal and tibial branches exposed and ligated with 5-0 silk suture, while special care was taken to avoid damage to the sural nerve. Approximately 2 mm of the nerve segments below the ligature was transected from both the branches. 5 rats were tested for each group (Control Group and STX-Liposome Treatment Group) in this study. Control group received skin incision and muscle layer separation, but no nerve injury. Rats in the liposome treatment group received 0.3 ml of the STX formulation as a nerve block injection ipsilateral to the SNI procedure, immediately after the surgery. Animals that did not receive liposomal STX did not receive any other forms of treatment. All nerve block injections were performed using a 23-gauge needle. The needle was introduced postero-medial to the greater trochanter, pointing in an antero-medial direction. On contact with bone, the needle was withdrawn approximately 1 mm and 0.3 mL of liposome formulation injected.

Behavioral Tests for Tactile and Thermal Responsiveness

Hind-limb tactile responsiveness to Von-Frey filaments (Stoelting Co, Wood Dale, Ill.) was measured on all animals at least 2-3 times a week for 60 days. As previously described in Shankarappa, et al., *"Forced-exercise delays neuropathic pain in experimental diabetes: effects on voltage-activated calcium channels"*, J. Neurochem., 118: 224-236(2011), following acclimatization to an enclosure with wire mesh bottom, calibrated Semmes Weinstein monofilaments (Stoelting Co, Wood Dale Ill.) were applied to the lateral plantar surface of rats. Filaments were applied individually to each hind limb for a period of 8 seconds, with sufficient force to cause slight buckling of the monofilament. The pattern of filament selection was based on the Up-Down method of Dixon, where testing began with a 2 g filament followed by a lower or higher weight filament depending on a positive or negative paw response respectively (see Chaplan, et al., "Quantitative assessment of tactile allodynia in the rat paw", Journal of Neuroscience Methods, 53: 55-63 (1994)). A reflexive paw withdrawal or licking of the feet within the 8 second stimulus duration was considered a positive response. Filament mass required to elicit a 50% positive response rate was defined as the withdrawal threshold and calculated as previously described (Chaplan). The investigator remained blinded to the groups during the period of testing.

To determine the duration of STX-liposome induced nerve blocks, behavioral response to thermal stimulus was evaluated using a modified hotplate, as reported previously by Kohane, et al., "A re-examination of tetrodotoxin for prolonged duration local anesthesia", Anesthesiology, 89: 119-131 (1998). Briefly, towel restrained rats were held over a 56 C pre-heated hot plate (IITC Inc., Woodland Hills, Calif.) and the plantar surface of the hind-paws sequentially placed on the heated plate. The time required for the animal to retract its foot was recorded as the withdrawal latency. Animals that did not withdraw their foot after 12 seconds were removed from the hot plate by the experimenter to prevent heat-mediated injury. A withdrawal response of more than 6 seconds (50% of maximal withdrawal latency) was considered a nerve block. Measurements were repeated three times with a 10 second pause between each test.

The experimenter was blinded as to what treatment specific rats were receiving.

The duration of thermal nociceptive block was calculated as the time required for thermal latency to return to a value of 7 seconds from a higher value; 7 seconds is the midpoint between a baseline thermal latency of ~2 seconds in adult rats, and a maximal latency of 12 seconds.

To test motor blockade in STX-liposome treated, non-SNI animals, the extensor postural thrust of each animal was tested by sequentially placing each hind paw on a digital weighing scale and measuring the maximum amount of weight the animal could bear without its ankle touching the weighing surface. The duration of motor block was defined as the time required for weight bearing to return halfway to normal from maximal block (<20 g of weight borne) (see Kohane 1998). The halfway point for each rat was defined as [(highest weight borne by either leg)–(lowest weight borne by blocked leg)]/2+(lowest weight borne by blocked leg).

Nerve Conduction Measurements

For assessing the effect of STX-liposomes on nerve function, evoked compound muscle action potential latencies and amplitudes from the sciatic nerve at the peak of nerve block, as characterized by the thermal paw withdrawal test (Day 4 post STX-liposome treatment) were measured. (see Shankarappa 2011) Briefly, rats were anesthetized by inhalation of 2% isoflurane in oxygen, and body temperature maintained with the aid of a heating pad. Sciatic nerve was stimulated at the ankle or at the sciatic notch via pin electrodes using a supra-maximal square pulse (24.9 mA, 0.05 ms, 1 Hz), while the recording electrode was placed in the plantaris muscle of the feet. Evoked responses were recorded. Conduction in the proximal and distal segments of the nerve was evaluated by measuring the M and H wave latencies.

Real Time PCR

Total DRG RNA samples underwent reverse transcription with SuperScript III (Invitrogen) following the manufacturer's procedure. Real-time PCR reactions for each sample were run in duplicate using 100 ng of cDNA in Taqman gene expression assays (Applied Biosystems) according to the manufacturer's instructions. Real time PCR was performed using Applied Biosystems' Step One equipment and program. The relative amount of specifically amplified cDNA was calculated using the delta-CT method (Vandesompele, et al., Genome biology, 3(7):RESEARCH0034-1-0034.11 (2002); Hoebeeck, et al., Laboratory investigation; A Journal of Technical Methods and Pathology, 85(1):24-33(2005)). The Applied Biosystems primers used are as follows: GAPDH: Rn99999916_S1, β-actin: Rn00667869_m1; Gadd45 α: Rn00577049_m1; ATF3: Rn00563784_m1; Cacna2d1: Rn01442580_m1; Smagp: Rn00788145_g1.

Statistics

Data are presented as means±standard deviations (n=5). To take multiple comparisons into account, all statistical comparisons were done with the Tukey-Kramer test, using InStat software (GraphPad, San Diego Calif.). A P-value <0.05 was considered to denote statistical significance.

Results

Figure 1A:
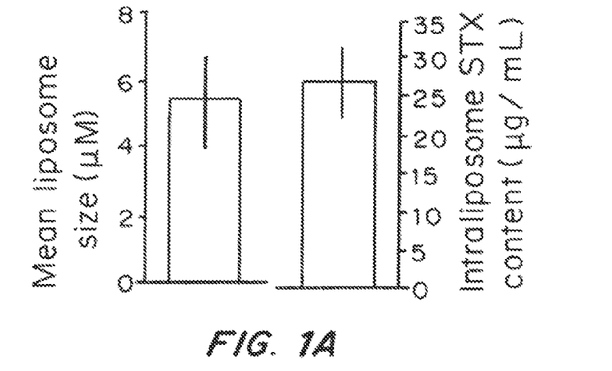
Figure 1B:
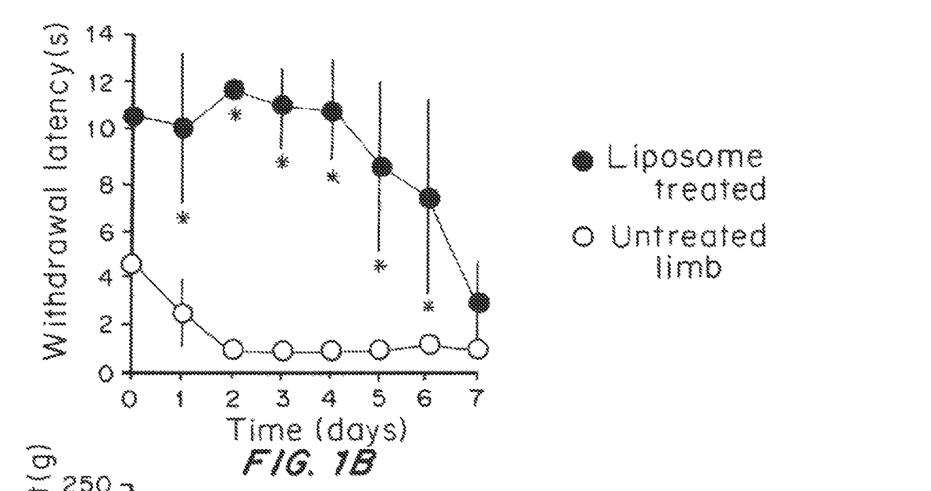
Figure 1C:
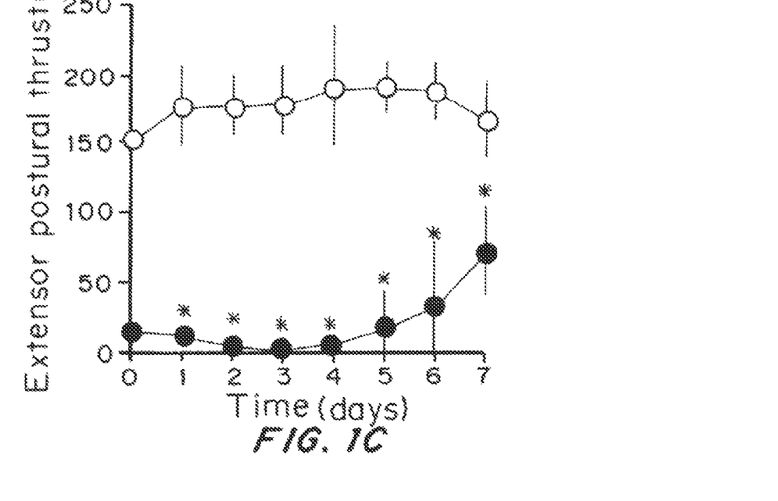
Figure 2:
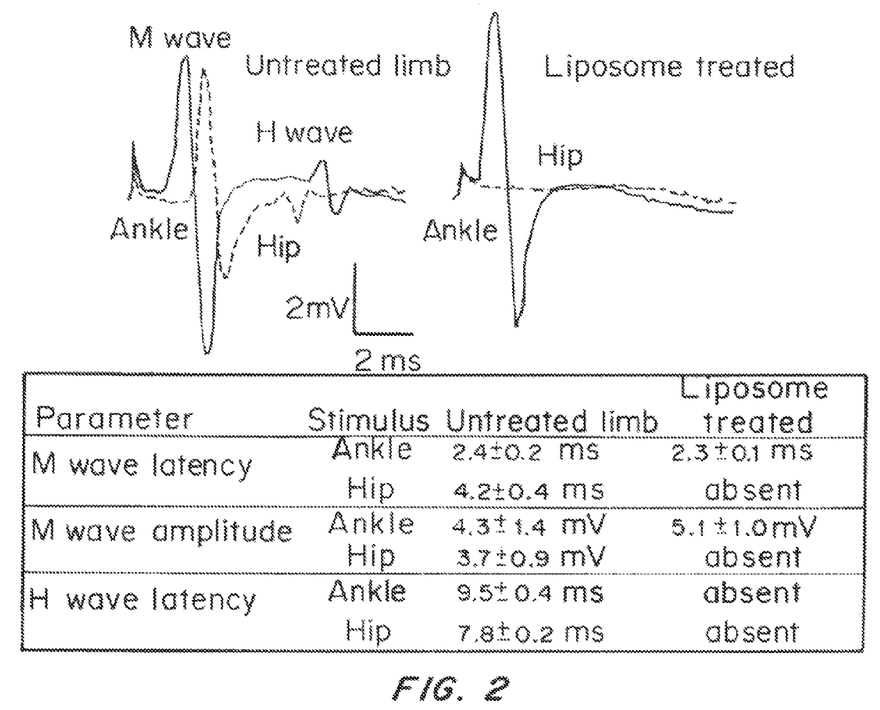
Figures 3A, 3B:
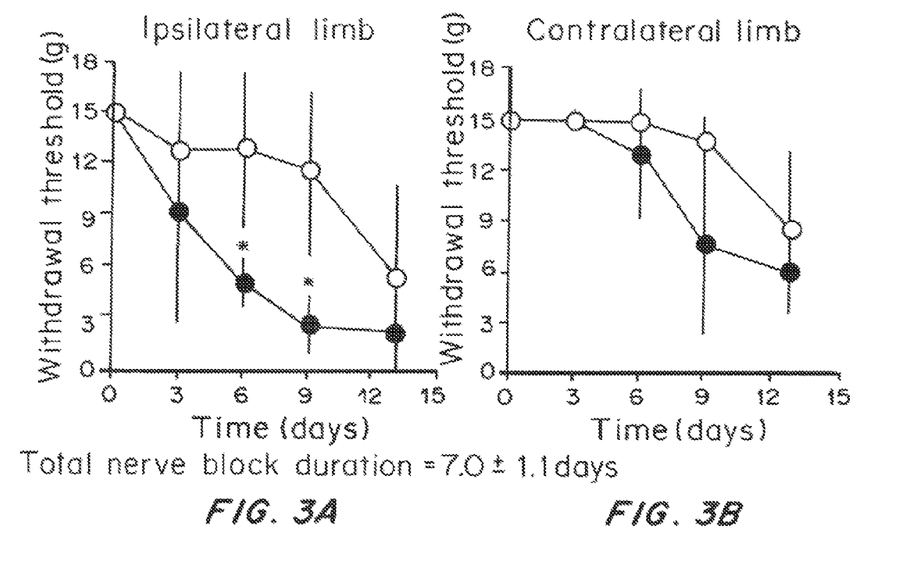
Figure 4A:
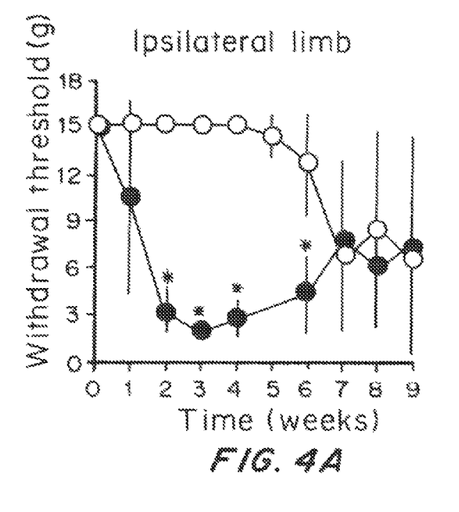
Figure 4B:
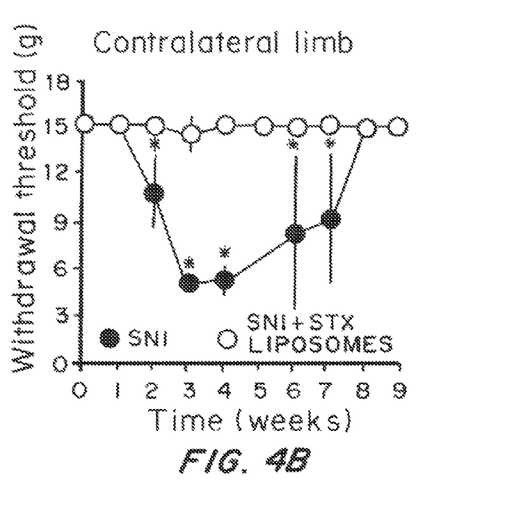
Figure 4C:
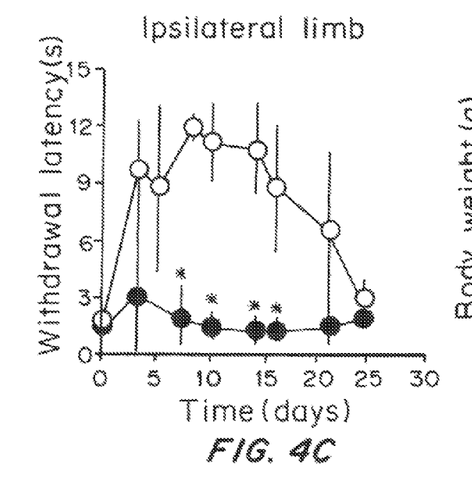
Figure 4D:
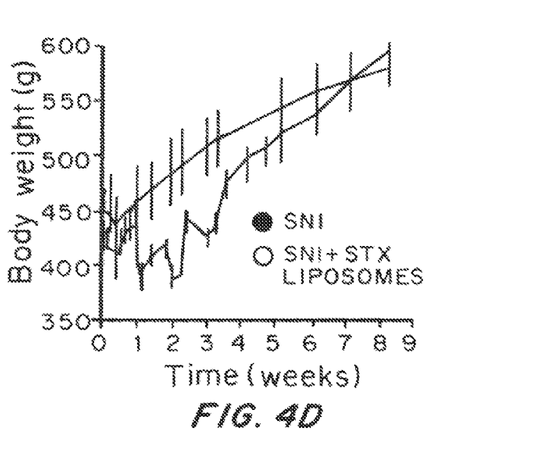

As shown on FIG. 1A, the mean liposome size was determined to be 5.2±1.3 microns, and the mean intraliposome STX content (μg/ml) was determined to be 27±4 (μg/ml).

When the rats were administered a single 0.3 ml dose of the saxitoxin liposomes, the liposomes produced up to 6 days of motor and sensory nerve block without producing local nerve injury. (See FIG. 1B, Sensory block duration and FIG. 1C, motor block duration).

Stained sections of the sciatic nerve from STX-L treated and untreated limb demonstrated no signs of inflammation or injury, while transmission electron microscopy imaging confirmed normal nerve morphology in response to STX-L treatment (data not shown).

STX-L produced complete localized nerve conduction block. On electrical stimulation at the hip, nerve conduction recordings in rats treated with STX-L demonstrated complete loss of 'M' and 'H' wave, while electrical stimulation at the ankle resulted only in the absence of the 'H' wave, suggesting very localized nerve block at the region of the hip.

The Table in FIG. 2 shows that STX-L treatment does not affect function in the nerve segment distal to the block.

As shown in FIGS. 3A and B, a single dose of the STX liposome formulation was ineffective at preventing or delaying the onset of neuropathic pain in the SNI model, where the nerve block was approximately 7 days in duration. SNI rats administered a single dose of STX-L developed ipsilateral hind limb sensitivity immediately after the nerve block wore off, while the contralateral limb showed no effect in response to STX-L treatment.

In contrast to the data in FIG. 3A, the dosing regimen used to produce a significantly longer nerve block of approximately 18 days was sufficient to delay the onset of neuropathic pain in the SNI rats. This is highlighted by the date in FIG. 4A. A prolonged nerve block of approximately 18 days in duration was obtained by administering three 0.3 ml doses of STX-L. Each dose was administered after the effect of the previous dose showed signs of waning. The nerve block duration was calculated using the data in FIG. 4C.

As shown in FIG. 4A, STX-L delays the onset of tactile hypersensitivity (hyperalgesia) in the ipsilateral hindlimb by 4 weeks (grey bar indicates the duration of nerve block as calculated from FIG. 4C). FIG. 4B shows that in the contralateral limb, the administration of 3 consecutive doses of STX-L completely prevented the onset of tactile hypersensitivity.

FIG. 4 D shows that body weight gain in rats that received STX-L showed moderate decrease during STX-L treatment, but recovered soon after.

Figure 5A:
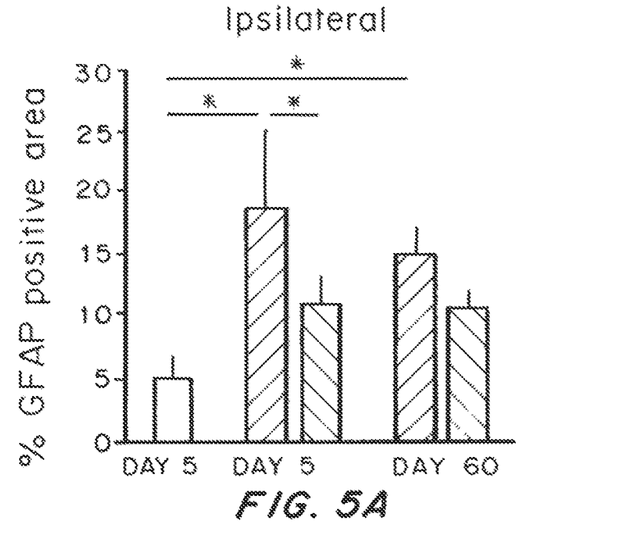
Figure 5B:
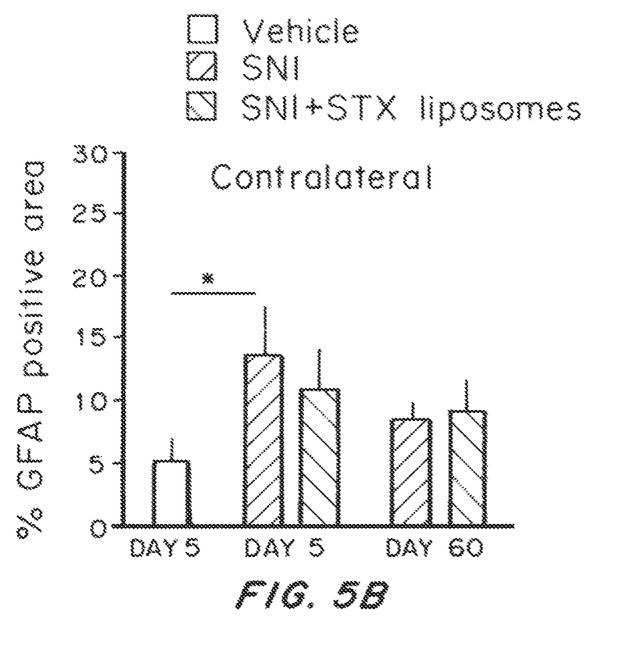

The data in FIGS. 5A and B demonstrate that STX-L treatment attenuates the neuropathic pain associated astrocyte response in the lumbar spinal cord.

Lumbar spinal cord harvested from SNI animals showed increased surface area of green fibrillary acidic protein (GFAP), an indicator of astrocyte activation, while STX-L treated SNI animals demonstrated an attenuated response at post-operative days 5 and 60 in the ipsilateral limb. The bar graphs in FIGS. 5A and B provide quantified results obtained from image analysis techniques.

Real Time PCR

To further assess the presence or absence of nerve injury 5 days after injection and 2 months (60 days) after the first injection, real time PCR was used to study the expression of the following genes: Gadd45a (Befort, et al., *Eur J Neurosci.*, 18(4):911-922 (2003)), ATF3 (Nakagomi, et al., *J Neurosci.*, 23(12):5187-5196 (2003); Song, et al., *Exp Neurol.*, 209(1): 268-278 (2008)), Cacna2d1 (Luo, et al., *J Pharmacol Exp Ther.*, 303(3):1199-1205 (2002); Newton, et al., *Brain Res Mol Brain Res.*, 95(1-2):1-8 (2001)) whose expression is altered by nerve injury, using RNA from the dorsal root ganglia of animals that received nerve blocks (n=5 in each group).

Expression was normalized to GAPDH as an internal control. Additional genes that were tested were: Ppia, Htr3a, Scn11a, Npy, Gal, Vip, C1qb, Jun, and RT1Db1.

The results for the ipsilateral and contralateral limbs are provided in Table 1 below.

TABLE 1

| | | | Ppia | Cacna2d1 | Htr3a | Scn11a | Npy | Gal | Vip |
|---|---|---|---|---|---|---|---|---|---|
| | | | | | Ipsilateral | | | | |
| 5D | STX lipo | | −1.1 ± 0.03 | −1.9 ± 0.2 | −2.0 ± 0.3 | −2.2 ± 0.5 | −2.3 ± 2.6 | −1.3 ± 0.2 | −4.8 ± 3.0 |
| | SNI | | 0.1 ± 1.1 | 3.2 ± 0.5 | −2.2 ± 0.1 | −2.5 ± 0.7 | 38.4 ± 12.8 | 45.3 ± 14.1 | 144.4 ± 42.4 |
| | STX lipo + SNI | | −1.0 ± 0.06 | 2.2 ± 1.0 | −3.6 ± 1.6 | −4.4 ± 2.6 | 47.8 ± 20.3 | 34.2 ± 16.7 | 115.6 ± 44.7 |
| 2M | SNI | | −0.01 ± 1.2 | 3.3 ± 0.8 | −0.7 ± 1.35 | −0.6 ± 1.1 | 19.6 ± 6.0 | 10.2 ± 5.6 | 202.2 ± 113.1 |
| | STX lipo + SNI | | 1.1 ± 0.05 | 1.9 ± 0.7 | −1.7 ± 0.5 | −2.7 ± 1.4 | 48.7 ± 10.2* | 13.6 ± 0.9 | 155.6 ± 49.0 |
| | | | | | Contralateral | | | | |
| 5D | STX lipo | | −1.1 ± 0.05 | −2.1 ± 0.8 | −1.8 ± 0.6 | −2.1 ± 0.8 | −1.1 ± 2.3 | −1.4 ± 0.2 | −2.5 ± 2.8 |
| | SNI | | −0.2 ± 1.1 | −1.5 ± 0.3 | −1.5 ± 0.4 | −1.9 ± 0.6 | −2.5 ± 1.0 | −1.4 ± 0.3 | −3.2 ± 2.1 |
| | STX lipo + SNI | | −0.6 ± 0.9 | −1.3 ± 0.1 | −1.3 ± 0.1 | −1.4 ± 0.1 | 0.4 ± 1.7 | 0.7 ± 0.9 | −1.0 ± 1.2 |
| 2M | SNI | | 0.4 ± 1.1 | 0.1 ± 1.3 | 0.5 ± 1.0 | −0.6 ± 1.3 | 0.8 ± 1.5 | −1.4 ± 0.2 | 2.6 ± 4.5 |
| | STX lipo + SNI | | −0.5 ± 1.0 | −9.9 ± 4.6* | −3.6 ± 0.3* | −15.6 ± 5.4* | −0.2 ± 4.6 | −3.1 ± 0.7* | −4.8 ± 2.0* |

| | | | C1qb | Jun | RT1Db1 | Gadd45a | Atf3 |
|---|---|---|---|---|---|---|---|
| | | | | Ipsilateral | | | |
| | 5D | STX lipo | 0.2 ± 1.4 | −1.4 ± 0.2 | −1.5 ± 0.2 | −1.2 ± 0.2 | −0.9 ± 1.4 |
| | | SNI | 7.9 ± 1.3 | 2.8 ± 0.2 | 3.7 ± 1.2 | 3.9 ± 0.6 | 37.2 ± 4.1 |
| | | STX lipo + SNI | 5.5 ± 2.2 | 2.0 ± 0.7 | 1.6 ± 1.6 | 4.0 ± 1.2 | 26.2 ± 10.7 |
| | 2M | SNI | 4.2 ± 2.6 | 2.6 ± 0.4 | 3.3 ± 1.8 | 2.6 ± 0.6 | 19.8 ± 7.3 |
| | | STX lipo + SNI | 3.8 ± 1.4 | 2.1 ± 0.6 | 3.3 ± 1.4 | 3.1 ± 0.2 | 17.7 ± 4.9 |
| | | | | Contralateral | | | |
| | 5D | STX lipo | 1.7 ± 0.6 | −1.6 ± 0.7 | 0.4 ± 1.4 | −1.3 ± 0.1 | −2.4 ± 1.1 |
| | | SNI | −0.1 ± 1.3 | −1.0 ± 1.2 | −1.2 ± 0.1 | −1.3 ± 0.05 | −1.5 ± 0.3 |
| | | STX lipo + SNI | 1.1 ± 1.2 | −1.5 ± 0.2 | −0.2 ± 1.3 | −1.5 ± 0.2 | −0.2 ± 1.2 |
| | 2M | SNI | 1.1 ± 1.5 | 0.6 ± 1.2 | 1.1 ± 0.2 | −0.003 ± 1.2 | 1.9 ± 0.5 |
| | | STX lipo + SNI | −2.6 ± 1.2 | −7.9 ± 2.6* | −1.8 ± 1.0 | −1.4 ± 0.09 | −7.5 ± 2.1* |

As shown by the data in Table 1, STX-L treatment does not affect SNI induced changes in gene expression in dorsal root ganglion neurons.

The data demonstrate that administration of STX in these liposomes, when administered in a suitable dosing regimen to achieve a sufficiently long nerve block, was effective at considerably delaying the onset of chronic neuropathic pain in the treated limb. In contrast, without the liposome treatment, the rats developed pain almost a month earlier. Further, in contrast, when a shorter nerve block was administered (i.e. approximately 7-8 days in duration), the rats also developed neuropathic pain within days of the termination of the nerve block.

We claim:

1. A method of providing nerve blockade comprising injecting to a site in need thereof in an individual with neuropathic pain a composition comprising a controlled release system selected from the group consisting of liposomes, micelles, micoparticles and nanoparticles, the system releasing a site 1 sodium channel blocker in combination with a glucocorticoid, providing an effective amount for at least 8 days, in the absence of local toxicity, to delay onset of neuropathic pain following the blockade.

2. The method of claim 1, wherein the controlled release system is liposomes.

3. The method of claim 2, wherein the controlled release system is liposomes and the site 1 sodium channel blocker and glucocorticoid is encapsulated in the liposomes.

4. The method of claim 1, wherein the site 1 sodium channel blocker is selected from the group consisting of tetrodotoxin (TTX), saxitoxin (STX), decarbamoyl saxitoxin, neosaxitoxin, and the gonyautoxins.

5. The method of claim 4, wherein the site 1 sodium channel blocker is neosaxitoxin.

6. The method of claim 1, wherein the composition comprises an effective amount of a glucocorticoid selected from the group consisting of dexamethasone, cortisone, hydrocortisone, prednisone, beclomethasone, betamethasone, flunisolide, methyl prednisone, para methasone, prednisolone, triamcinolome, alclometasone, amcinonide, clobetasol, fludrocortisone, diflurosone diacetate, fluocinolone acetonide, fluoromethalone, flurandrenolide, halcinonide, medrysone, and mometasone, and pharmaceutically acceptable salts and mixtures thereof, to enhance nerve block in the absence of local toxicity as compared to the sodium channel blocker alone.

7. The method of claim 6, wherein the site 1 sodium channel blocker is STX and the glucocorticoid is dexamethasone.

8. The method of claim 3, wherein the liposomes are formed from one or more lipids selected from the group consisting of 1,2-distearoyl-sn-glycero-3 phosphocholine (DSPC), 1,2-distearoyl-sn-glycero-3-phoshatidylglycerol (DSPG) and cholesterol.

9. The method of claim 8, wherein the liposomes comprise DSPC:DSPG:cholesterol:dexamethasone in a molar ratio of 3:1:2:0.0001.

10. The method of claim 1, wherein the composition is administered in more than one consecutively administered dose.

11. The method of claim 1, comprising administering two or three times a composition comprising a site 1 sodium channel blocker in combination with a glucocorticoid, in a liposomal controlled release system, to provide a nerve blockade for longer than approximately 18 days in duration in the absence of local toxicity.

12. The method of claim 1, wherein the controlled release system is a liposome, and wherein the composition is stored in a vial as a dry powder, or suspended in an aqueous solution for injection.

13. The method of claim 1 comprising administering a therapeutically effective amount of a composition comprising a site 1 sodium channel blocker and glucocorticoid in an effective amount to provide a nerve blockade for longer than 10 days in duration in the absence of local toxicity.

14. The method of claim 1, wherein the controlled release system is selected from the group consisting of micelles, microparticles and nanoparticles.

15. The method of claim 11, wherein the site 1 sodium channel blocker is selected from the group consisting of tetrodotoxin (TTX), saxitoxin (STX), decarbamoyl saxitoxin, neosaxitoxin, and the gonyautoxins.

16. The method of claim 15, wherein the site 1 sodium channel blocker is neosaxitoxin.

17. The method of claim 11, wherein the composition comprises an effective amount of a glucocorticoid selected from the group consisting of dexamethasone, cortisone, hydrocortisone, prednisone, beclomethasone, betamethasone, flunisolide, methyl prednisone, para methasone, prednisolone, triamcinolome, alclometasone, amcinonide, clobetasol, fludrocortisone, diflurosone diacetate, fluocinolone acetonide, fluoromethalone, flurandrenolide, halcinonide, medrysone, and mometasone, and pharmaceutically acceptable salts and mixtures thereof, to enhance nerve block in the absence of local toxicity as compared to the sodium channel blocker alone.

18. The method of claim 17, wherein the site 1 sodium channel blocker is neosaxitoxin and the glucocorticoid is dexamethasone.

19. The method of claim 11, wherein the liposomes are formed from one or more lipids selected from the group consisting of 1,2-distearoyl-sn-glycero-3 phosphocholine (DSPC), 1,2-distearoyl-sn-glycero-3-phoshatidylglycerol (DSPG) and cholesterol.

20. The method of claim 19, wherein the liposomes comprise DSPC:DSPG:cholesteroLdexamethasone in a molar ratio of 3:12:0.0001.

21. The method of claim 11, wherein the composition is administered in at least three doses.

22. The method of claim 1 wherein the composition is administered in at least two doses.

23. The method of claim 1 wherein the composition is administered in at least three doses.

* * * * *